United States Patent [19]

Redmore et al.

[11] 4,409,151

[45] Oct. 11, 1983

[54] N,N-DIMETHYLENE PHOSPHONIC ACIDS OF ALKYLENE DIAMINES

[75] Inventors: Derek Redmore, Webster Groves; William S. Paley, Maryland Heights, both of Mo.

[73] Assignee: Petrolite Corporation, St. Louis, Mo.

[21] Appl. No.: 334,847

[22] Filed: Dec. 28, 1981

Related U.S. Application Data

[62] Division of Ser. No. 201,866, Oct. 29, 1980, Pat. No. 4,330,487.

[51] Int. Cl.$^3$ ............................................. C07F 9/38
[52] U.S. Cl. ............................................. 260/502.5 E
[58] Field of Search ..................................... 260/502.5

[56] References Cited

U.S. PATENT DOCUMENTS 2,599,807   6/1952   Bersworth .................... 260/502.5
3,288,846  11/1966   Irani et al. .................... 260/502.5

Primary Examiner—J. E. Evans
Attorney, Agent, or Firm—Sidney B. Ring; Hyman F. Glass; Leon Zitver

[57] ABSTRACT

This invention relates to a process of preparing N,N'-disubstituted methylene phosphonic acids by reacting α,ω-alkylene diamines with essentially 2 equivalents of formaldehyde and phosphorus acid based on replaced nitrogen-bonded hydrogens.

This invention also relates to compositions formed by the process and to the uses for these compositions such as for inhibiting scale, etc.

3 Claims, No Drawings

N,N-DIMETHYLENE PHOSPHONIC ACIDS OF ALKYLENE DIAMINES

This is a division of application Ser. No. 201,866, filed Oct. 29, 1980, now U.S. Pat. No. 4,330,487.

In prior art processes for reacting α,ω alkylene diamines with formaldehyde and phosphorous acid a mixture of N-substituted methylene phosphonic acids is formed. For example, when $NH_2(CH_2)_nNH_2$ is reacted with formaldehyde ($CH_2O$) N-substitution is non selective with phosphorous acid ($H_3PO_3$) so that substitution of all of the nitrogen bonded hydrogens occurs so as to form a mixture of methylene phosphonic acids.

Thus, the N,N-disubstituted methylene phosphonic acids, such as of the formula

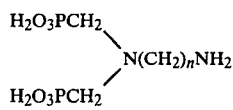

have never been prepared, isolated and identified.

We have now discovered a process of preparing these novel compounds by reacting α,ω alkylene diamines with formaldehyde and phosphorous acid so as to selectively orient substitution on the same nitrogen group according to the following equation:

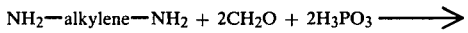

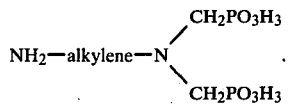

The alkylene group is, for example, $-(CH_2)_n-$, where n is at least 2, such as 2–20 or more, but preferably 2 to 10, but most preferably 2 to 6.

To achieve this result each mole of the diamine is reacted with 2 equivalents of formaldehyde and phosphorous acid (based on replaceable nitrogen bonded hydrogens). Stated another way, by employing the process of this invention, disubstitution which occurs on the same nitrogen atom, i.e. N,N-disubstitution, as contrasted to N,N'-substitution which occurs on different nitrogen atoms, to form mixtures thereof.

The reaction of this invention is phosphoromethylation carried out as following, according to the well known Mannich reaction:

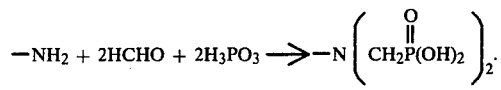

The Mannich reaction is quite exothermic and initial cooling will generally be required. Once the reaction is well under way, heat may be required to maintain refluxing conditions. While the reaction will proceed at temperatures over a wide range, i.e., from 80° to 150° C., it is preferred that the temperatures of the reaction medium be maintained at the refluxing temperature. The reaction is preferably conducted at atmospheric pressure, although sub-atmospheric and super-atmospheric pressures may be utilized if desired. Reaction times will vary, depending upon a number of variables, but the preferred reaction time is 2½ to 3½ hours.

Although the phosphorous acid and the formaldehyde may be added in either order, or together to the reaction mixture, it is preferred to add the phosphorous acid to the diamine and then to slowly add the formaldehyde under refluxing conditions. Essentially 2 equivalents of the formaldehyde and phosphorous acid are added per mole of diamine.

It is preferred that the reaction be carried out in an aqueous solution containing from about 40 to about 50% of the reactants. Preferred conditions for the Mannich reaction include refluxing conditions and a pH of less than 2 and preferably less than 1.

EXAMPLE 1

Preparation of ethylenediamine-N,N-bis(methylene phosphonic) acid

Ethylenediamine (6.0 g; 0.1 mole) was placed in a four necked flask, fitted with a thermometer, condenser, addition funnel, and magnetic stirring bar. To the amine was added phosphorous acid (16.4 g; 0.2 mole) dissolved in 50 ml of water and 50 ml of conc. hydrochloric acid. The mixture was stirred and heated to reflux (~103° C.) before 37% w/w formaldehyde (18.0 ml; 0.22 mole) was added dropwise over one hour. After the addition the mixture was heated under reflux for two additional hours.

Ion exchange chromatography on AG 50W-X8 (200 mesh) separated the diphosphonic acid by elution with 2.0 N HCl (Yield 18.6 g ~75%).

Anal. Calcd for $C_4H_{14}N_2O_6P_2$: N, 11.29; P, 25.00. Found: N, 11.31; P, 25.28.

Carbon ($^{13}C$) and phosphorus ($^{31}P$) nuclear magnetic resonance spectra were consistent with N,N-diphosphonic acid structure as shown:

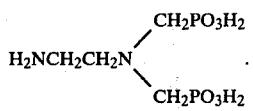

EXAMPLE 2

Preparation of 1,3-propylenediamine-N,N-bis(methylene phosphonic) acid

To 1,3-Propylenediamine (7.4 g; 0.1 mole) was added water (50 ml), hydrochloric acid (50 ml) and phosphorous acid (16.4 g; 0.2 mole). The resulting solution was heated to reflux with stirring and aqueous formaldehyde (18 ml; 0.22 mole) was added dropwise during 1 hour. Heating was continued for two hours after completion of the addition. Evaporation of the aqueous acid yielded 1,3-propylenediamine-N,N-bis(methylene phosphonic) acid. An analytically pure sample was obtained by ion exchange chromatography and crystallization from water/ethanol.

Anal. Calcd for $C_5H_{16}N_2O_6P_2$: N, 10.69; P, 23.67. Found: N, 10.06 P, 23.45.

Carbon and phosphorus nmr spectra were consistent with the structure below:

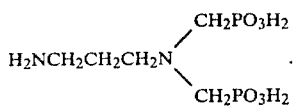

EXAMPLE 3

Preparation of 1,6-hexamethylenediamine-N,N-bis(methylene phosphonic) acid

To 1,6-hexamethylenediamine (17.4 g; 0.15 mole) was added water (60 ml), hydrochloric acid (60 ml) and phosphorous acid (24.6 g; 0.3 mole). The resulting solution was heated at reflux during the dropwise addition of aqueous formaldehyde, (28.5 ml; 0.35 mole) over 1 hour. Heating was continued for a further 2 hours after which the aqueous acid was removed under vacuum. The resulting diphosphonic was obtained in analytically pure form by ion exchange chromatography and crystallization from water/ethanol.

Anal. Calcd for $C_8H_{20}N_2O_6P_2.2K$: N, 7.37; P, 16.32
Found: N, 7.39; P, 15.84

Carbon and phosphorus nmr were consistent with the N,N-diphosphonic acid structure as shown:

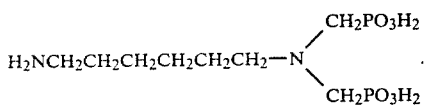

USE AS SCALE INHIBITOR

Most commercial water contains alkaline earth metal cations, such as calcium, barium, magnesium, etc., and anions such as bicarbonate, carbonate, sulfate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction products, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating or sequestering agents, so that the solubility of their reaction products is not exceeded. Generally, this approach requires many times as much chelating or sequestering agent as cation present, and the use of large amounts of treating agent is seldom desirable or economical.

More than 25 years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound, to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which they act as threshold inhibitors. Therefore, one could also define "threshold" concentrations as all concentrations of threshold active compounds below that concentration at which this turbid zone or precipitate is formed. Generally the threshold active compound will be used in a weight-ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylenediamine tetracetic acid salts are powerful sequesterants but have no threshold activities.

We have now discovered a process for inhibiting scale such as calcium, barium and magnesium carbonate, sulfate, silicate, etc., scale which comprises employing threshold amounts of the compositions of this invention.

Scale formations from aqueous solutions containing an oxide variety of scale-forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm and are preferably used in concentrations of less than 25 ppm.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to believe that this is the minimum effective concentration. The scale inhibitors of the present invention are effective in both brine, such as sea water, and acid solutions.

SCALE INHIBITOR TESTS

The scale inhibiting properties of phosphonic acids of this invention were evaluated by the seeded crystal growth technique.

This technique has been described in "Journal of Colloid and Interface Science," volume 52, 593–601 (1975) for $CaSO_4.2H_2O$ and for $BaSO_4$ in "Journal of Colloid and Interface Science," volume 52, 582–592 (1975).

Calcium Sulfate

The technique involves the addition of a fixed quantity of seed crystals to a metastable solution of the inorganic salt followed by periodic analysis for changes in the salt concentration. Seeded crystal growth experiments were conducted in a water-jacketed beaker containing 245 ml of a metastable $CaSO_4$ solution. The metastable solution was prepared by carefully combining equimolar quantities of $CaCl_2$ and $Na_2SO_4$ such that the final $CaSO_4$ solution would be $5.0 \times 10^{-2}$ M. Solution pH was controlled by the addition of buffers at a total conjugate acid/base concentration of $2.0 \times 10^{-3}$ M, a concentration at which the influence of the buffering components on the rate of crystal growth was proved to be negligible. Inhibitors were added after the addition of $CaCl_2$, but before the addition of $Na_2SO_4$, as dilute solutions in water. At thermal equilibrium, crystal growth was initiated by adding to the well-stirred metastable solution, 715 mg of $CaSO_4.2H_2O$ seed crystals evenly dispersed in 5.0 ml of a saturated $CaSO_4$ solution. Thereafter, aliquots of the reaction mixture were removed at periodic intervals, filtered through a prewashed 0.45 μm microporous membrane, and analyzed for calcium ion concentration. Calcium ion analyses were performed by titration with standard EDTA to the hydroxynaphthol blue endpoint.

The loss of calcium ion from solution with increasing reaction time obeys a second-order rate law. These rates are shown below:

| Inhibitor | Concentration | pH | Rate | Inhibition |
|---|---|---|---|---|
| Blank | | 4 | 3.6 mole $^{-1}$min$^{-1}$ | — |
| Example 1 | 5 ppm | 4 | 1.6 mole $^{-1}$min$^{-1}$ | 56% |
| Example 1 | 10 ppm | 4 | 0.9 mole $^{-1}$min$^{-1}$ | 75% |
| Hydroxyethylidene Diphosphonic Acid | 5 ppm | 4 | 2.4 mole $^{-1}$min$^{-1}$ | 33% |
| Example 1 | 5 ppm | 7 | 0.4 mole $^{-1}$min$^{-1}$ | 89% |
| Hydroxyethylidene Diphosphonic acid | 5 ppm | 7 | 2.4 mole $^{-1}$min$^{-1}$ | 33% |

Barium Sulfate

Either a 1.5 ml or a 4.5 ml quantity of 0.01 M $BaCl_2$ solution was placed in a 400 ml water jacketed cell containing 280 ml deionized water. The magnetically stirred solution was allowed to come into thermal equilibrium with water circulated through the outer cell jacket (25°±0.1° C.). Either a 1.5 ml or a 4.5 ml quantity of 0.01 M $Na_2SO_4$ solution was then added at a rate that was sufficiently slow to prevent localized nucleation. After adjusting the solution pH to the desired value with either 0.01 M HCl or 0.01 M NaOH, sufficient water was added to bring the total volume to 298 ml. The metastable solution was then seeded with 2.0 ml of the seed crystal suspension to induce crystal growth. The resulting change in conductivity was recorded as a function of time using a Radiometer CDM3 conductivity meter equipped with a Radiometer PP1042 double platinum electrode. Inhibited crystal growth was studied in like manner, with inhibitor added before the addition of $Na_2SO_4$.

The loss of barium ion from solution with increasing reaction time obeys a second order rate law. These rates shown below demonstrate the effective inhibition by the compositions of this invention.

| Inhibitor | Concentration | pH | Rate | Inhibition |
|---|---|---|---|---|
| none | = | 7 | $8 \times 10^{-3}$m$^{-1}$min$^{-1}$ | — |
| Example 1 | 2 ppm | 7 | $2 \times 10^{-3}$m$^{-1}$min$^{-1}$ | 75% |
| Example 1 | 5 ppm | 7 | $1 \times 10^{-3}$m$^{-1}$min$^{-1}$ | 88% |

The compositions of this invention are also useful as corrosion inhibitors.

Derivatives of the compositions of this invention can also be formed by reacting the amino group. For example, the compositions can be acylated to form

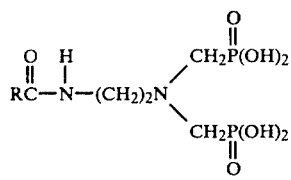

where R is any carboxylic moiety such as aliphatic, for example alkyl, alkenyl, etc., cycloalkyl, aryl, alkaryl, aralkyl, for example methyl, ethyl, undecyl, cyclohexyl, benzyl, phenyl, naphthyl.

They can be reacted with dicarboxylic acids such as maleic anhydride and maleic derivatives to form imides, etc.

In addition the compositions can be oxyalkylation, etc., with ethylene oxide, propylene oxide, etc. and mixtures thereof.

In addition salts of the phosphonic acid moiety can be formed such as sodium, potassium, ammonium, tetra alkylammonium, etc.

These derivatives are also useful as corrosion inhibitors, scale inhibitors, etc.

We claim:

1. A process of preparing an N,N-dimethylene phosphonic acid of the formula $$NH_2(CH_2)_nN(CH_2PO_3H_2)_2$$

where n=2-20, which comprises reacting in aqueous solution one mole of a diamine of the formula $$NH_2(CH_2)_nNH_2$$

where n has the aforesaid value, with essentially two equivalents each, based on nitrogen-bonded hydrogen, of formaldehyde and phosphorous acid, at a pH of less than 2 and a temperature from 80° to 150° C., the formaldehyde and phosphorous acid being added in either order or together to the diamine.

2. A process of preparing an N,N-dimethylene phosphonic acid of the formula $$NH_2(CH_2)_nN(CH_2PO_3H_2)_2$$

where n=2-20, which comprises reacting in aqueous solution one mole of a diamine of the formula $$NH_2(CH_2)_nNH_2$$

where n has the aforesaid value, with essentially two equivalents each, based on nitrogen-bonded hydrogen, of formaldehyde and phosphorous acid, at a pH of less than 2 and a temperature from 80° C. to 150° C., the formaldehyde being added to a mixture of the diamine and phosphorous acid.

3. The process of claim 2 wherein n=2-6.

* * * * *